(12) United States Patent
D'Alessio et al.

(10) Patent No.: US 6,283,933 B1
(45) Date of Patent: Sep. 4, 2001

(54) APPLICATOR FOR DISPENSABLE LIQUIDS

(75) Inventors: Keith R. D'Alessio, Cary; William M. Cotter, Raleigh, both of NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/219,851

(22) Filed: Dec. 23, 1998

(51) Int. Cl.[7] .......................... A61M 35/00; A46B 11/00; B43K 5/12
(52) U.S. Cl. .................. 604/3; 401/39; 401/132; 401/192; 401/196
(58) Field of Search .................. 604/1–3; 401/37–39, 401/132–135, 192, 196, 198; 22/541.1

(56) References Cited

U.S. PATENT DOCUMENTS

| | | |
|---|---|---|
| 1,893,997 | 1/1933 | Barksdale . |
| 2,721,858 | 10/1955 | Joyner et al. . |
| 3,254,111 | 5/1966 | Hawkins et al. . |
| 3,324,855 | * 6/1967 | Heimlich ............................ 604/2 |
| 3,527,841 | 9/1970 | Wicker et al. . |
| 3,559,652 | 2/1971 | Banitt et al. . |
| 3,667,472 | 6/1972 | Halpern . |
| 3,722,599 | 3/1973 | Robertson et al. . |
| 3,724,018 | 4/1973 | Sills . |

(List continued on next page.)

FOREIGN PATENT DOCUMENTS

| | | |
|---|---|---|
| WO 96/40797 | 12/1996 | (EP) . |
| 2690255 | 10/1993 | (FR) . |
| 2189398 | 10/1987 | (GB) . |
| 89/10745 | 11/1989 | (WO) . |
| 93/25196 | 12/1993 | (WO) . |

*Primary Examiner*—Dennis Ruhl
(74) *Attorney, Agent, or Firm*—Oliff & Berridge, PLC (57) ABSTRACT

A disposable applicator includes a generally tubular applicator body having a closed proximal end and an open distal end and a frangible vial inside. The proximal end is covered by a drying swab while the distal end is covered by an applicator swab that is in open communication with the interior of the applicator body. Within the applicator body is a frangible vial containing a biomedically useful liquid composition, such as an α-cyanoacrylate adhesive, a medicament, or both. The applicator is useful for applying liquid compositions to target sites such as tissue, particularly sites of topical pathology, such as stomatitis lesions.

44 Claims, 5 Drawing Sheets

U.S. PATENT DOCUMENTS

| | | | |
|---|---|---|---|
| 3,757,782 | * 9/1973 | Aiken | 604/2 |
| 3,792,699 | 2/1974 | Tobin et al. . | |
| 3,891,331 | * 6/1975 | Avery | 604/3 |
| 3,924,623 | * 12/1975 | Avery | 604/2 |
| 3,940,362 | 2/1976 | Overhults . | |
| 3,995,641 | 12/1976 | Kronenthal et al. . | |
| 4,148,318 | * 4/1979 | Meyer | 401/132 |
| 4,173,978 | * 11/1979 | Brown | 401/196 |
| 4,206,843 | 6/1980 | Rainey . | |
| 4,313,865 | 2/1982 | Teramoto et al. . | |
| 4,364,876 | 12/1982 | Kimura et al. . | |
| 4,430,013 | 2/1984 | Kaufman . | |
| 4,432,749 | * 2/1984 | Snyder et al. | 604/2 |
| 4,560,723 | 12/1985 | Millet et al. . | |
| 4,740,194 | * 4/1988 | Barbino et al. | 604/3 |
| 4,776,836 | 10/1988 | Stanley . | |
| 4,784,506 | * 11/1988 | Koreska et al. | 401/132 |
| 4,863,422 | 9/1989 | Stanley . | |
| 4,887,994 | * 12/1989 | Bedford | 604/1 |
| 4,957,385 | * 9/1990 | Weinstein | 604/3 |
| 5,035,348 | 7/1991 | Seifert . | |
| 5,100,028 | 3/1992 | Seifert . | |
| 5,259,835 | 11/1993 | Clark et al. . | |
| 5,288,159 | * 2/1994 | Wirt | 401/133 |
| 5,308,180 | * 5/1994 | Pournoor et al. | 401/132 |
| 5,328,687 | 7/1994 | Leung et al. . | |
| 5,435,660 | * 7/1995 | Wirt | 401/135 |
| 5,445,462 | * 8/1995 | Johnson et al. | 604/3 |
| 5,509,744 | * 4/1996 | Frazier | 604/3 |
| 5,514,371 | 5/1996 | Leung et al. . | |
| 5,514,372 | 5/1996 | Leung et al. . | |
| 5,575,997 | 11/1996 | Leung et al. . | |
| 5,582,834 | 12/1996 | Leung et al. . | |
| 5,624,669 | 4/1997 | Leung et al. . | |
| 5,658,084 | 8/1997 | Wirt . | |
| 5,690,958 | 11/1997 | McGrath . | |
| 5,709,866 | 1/1998 | Booras et al. . | |
| 5,762,494 | 6/1998 | Archambault . | |
| 5,782,801 | * 7/1998 | Caillouette | 604/3 |
| 5,791,801 | * 8/1998 | Miller | 604/3 |
| 6,090,397 | 7/2000 | Lee et al. . | |

* cited by examiner

APPLICATOR FOR DISPENSABLE LIQUIDS

BACKGROUND OF THE INVENTION

1. Field of the Invention

The invention relates to a disposable applicator, and more particularly to an applicator that can be used to apply a therapeutic or otherwise biomedically useful liquid composition to a surface, such as a biological tissue.

2. Description of Related Art

Numerous swabs and applicators for delivering biomedically useful compositions are known. Included among these are the flexible fluid dispensers disclosed in U.S. Pat. Nos. 5,035,348 and 5,100,028 to Seifert. Seifert discloses flexible fluid dispensers that include a top and bottom wall and a seal that seals the top wall to the bottom wall and is shaped to concentrate forces resulting from pressure generated by applying a force to the dispenser. The opening resulting from a break in the seal is proportional in size to the force applied to the dispenser. The applicator comprises a dispenser and a saturable end-piece. Force provided on the dispenser between two seals causes opening of one of the seals at a predetermined site. Fluid contained within the applicator flows into the saturable end-piece, which can be used to apply the fluid.

U.S. Pat. No. 3,757,782 to Aiken discloses a fluid pressurizable swab applicator for medicament. The applicator is a double swab-ended applicator comprising an encapsulated charge of solution sealed between the extreme ends of a flexible plastic tubular applicator rod. One or both ends of the swab applicator can be saturated during use with the encapsulated charge (a medicament, antiseptic, or like solution). Manual pinching of the tubular applicator rod ruptures temporary seal elements at both of the tube ends. No manipulation or fracturing of an ampoule-like part, or specific removal of another type of sealing element is entailed.

U.S. Pat. Nos. 4,863,422 and 4,776,836, both to Stanley, disclose a double ended swab applicator for applying a treating liquid. The applicator supplies heated treating liquids such as medicaments, antiseptics and lubricants for direct application to a particular region of a patient's body. As shown in detail in FIGS. 1–3, a liquid, such as a medicament, is contained in an inner lumen contained within a compressible and flexible synthetic plastic handle. Between the handle and the inner lumen is an outer lumen filled with a heat-generating material. Upon compression of the handle, the heat-generating material heats the liquid in the inner lumen. A frangible seal can then be ruptured by bending the applicator at the area around the frangible seal, allowing the liquid to flow into a compartment. The pressure produced by compression of the handle also ruptures a membrane and allows the liquid to flow into a swab. One membrane is non-rupturable, allowing a second swab to remain dry.

U.S. Pat. No. 4,430,013 to Kaufmnan discloses disposable swab articles comprising an applicator package having proximal ends and having a foam applicator pad and a backing member adjacent thereto. In use, the ends of the applicator package are pinched together, causing a receptacle to break open at a pre-weakened area, thus allowing the liquid within the receptacle to flow into a foam element. In an embodiment depicted in FIGS. 10 and 11, the applicator package has a sponge or foam swab applicator tip disposed at one end. The applicator further comprises a receptacle located within the handle that holds a liquid to be dispensed. The receptacle has a scored line located near the applicator tip that is a point of weakness for breaking the receptacle. Upon breaking of the receptacle at the scored line, the liquid within the receptacle flows out into the applicator tip. The disclosed applicator does not comprise a second sponge or foam swab at the end opposite the applicator tip end.

U.S. Pat. No. 5,690,958 to McGrath discloses a bactericidal agent dosage applicator comprising chlorhexadine gluconate contained within a manually-crushable glass ampoule. In one embodiment, shown in FIG. 2, an elongated cylindrical glass vial or ampoule is housed within an elongated, cylindrical, flexible, synthetic resin cover of a size to fully encase the vial. A porous applicator swab is fitted within one end of the applicator cover. To operate the applicator, the user crushes the vial by applying adequate force to the protective cover to break the side wall of the glass vial. The antiseptic solution released from the broken vial is quickly absorbed by the porous tip, thus permitting the user to apply the solution directly to the patient's skin. McGrath does not disclose a second porous tip on the other end of the applicator.

U.S. Pat. No. 3,324,855 to Heimlich discloses a surgical sponge stick for removal of excess fluids during surgical procedures. The sponge stick comprises a hollow handle with a first open end and a second perforated end. The perforated end is surrounded by a porous absorbent surgical sponge material. The sponge stick may be used in preparing a patient for surgery by incorporating an antiseptic solution within the stick. FIG. 4 discloses an embodiment wherein the liquid or solution to be applied is contained in a frangible cartridge disposed in the handle and retained therein by a stop secured inside the handle adjacent an open end. The frangible cartridge or ampoule is broken by squeezing or flexing the handle, allowing the liquid to flow into the sponge.

U.S. Pat. No. 5,445,462 to Johnson et al. discloses a liquid applicator with both upper and lower open ends and a porous material attached to a tip as part of one end. A closed, frangible ampoule is supported within the end that does not comprise the tip and contains a liquid to be dispensed. A cap is located at the end opposite the tip that is movable to fracture the ampoule and release its contents. The body of the applicator is preferably formed of a resilient material such as thin-walled plastic material or the like, and fluid is pressured through the tip onto the application point.

U.S. Pat. No. 5,658,084 to Wirt discloses an article useful as a dispenser for the application of a liquid. The article is an applicator that comprises a rupturable reservoir containing a solution, a hollow elongate member that has a major orifice at one end and contains the rupturable reservoir, deformable means contained within the hollow elongate member for supporting and protecting the reservoir until the liquid is to be dispensed, means for limiting the axial displacement of the deformable means, and means for rupturing the reservoir. The deformable means has an aperture through which at least a portion of the reservoir may be pushed. The means for rupturing the reservoir functions after at least a portion of the reservoir is pushed through the aperture in the deformable means. Upon rupture of the reservoir, the solution is applied through a foam sponge. The rupturable reservoir, or frangible ampoule, comprises a stress-concentrator between the ampoule neck portion and body portion to serve as a break point for the ampoule.

U.S. Pat. No. 5,308,180 to Pournoor et al. discloses an article for the application of a liquid to a surface. The article is a dispenser for application of a liquid to a surface that comprises a hollow elongate member that has a major orifice at one end, a flexible, porous layer disposed over the major orifice, a layer of sponge material disposed over the exterior surface of the porous layer, and a means of maintaining atmospheric pressure within the hollow elongate member while the liquid to be applied by the applicator is being dispensed. The flexible, porous layer of porous material is disposed over the first major orifice of the hollow elongate member, and is sandwiched between a flange and the foam sponge. The porous layer is disposed over the major orifice to control the flow of liquid out of the hollow elongate member and into the foam sponge.

It is also known to use adhesives in wound closure and covering. For example, U.S. Pat. No. 3,559,652 to Coover et al. discloses the use of cyanoacrylate adhesives to close wounds or incisions by applying the adhesive composition to one or both surfaces of the wound or incision, then holding the two surfaces together until the two surfaces are bonded. U.S. Pat. No. 3,667,472 to Halpern discloses a different method for wound closure wherein a cyanoacrylate adhesive is applied across two abutted tissue surfaces to form a bridge between the two surfaces. The tissue surfaces are held together until the adhesive forms a bond between the two surfaces. Other adhesive compositions and methods of wound closure are disclosed in, for example, U.S. Pat. No. 5,328,687 to Leung et al.; U.S. Pat. No. 3,527,841 to Wicker et al.; U.S. Pat. No. 3,722,599 to Robertson et al.; U.S. Pat. No. 3,995,641 to Kronenthal et al.; and U.S. Pat. No. 3,940,362 to Overhults.

A method for application of a topical cyanoacrylate tissue adhesive is disclosed in product literature accompanying Histoacryl® cyanoacrylate adhesive, which is commercially available from B. Braun Melsungen AG of Germany.

International Application No. PCT/US96/09575 to Closure Medical Corporation, published as International Publication No. WO 96/40797, discloses an applicator and tip for dispensing a polymerizable and/or cross-linkable material. The applicator includes a container holding a polymerizable andlor cross-linkable material, an optional plunger for forcing the material from the container, and an applicator tip having a portion thereof with a polymerization andlor cross-linking initiator. The tip is porous and absorbent or adsorbent. The polymerization or cross-linking initiator can be coated on an interior surface of the applicator in the case where the material is contained in a frangible vial within the applicator.

Although it is known to make and use applicators for dispensing medicinal or therapeutic liquids, none of the applicators currently known provide a disposable applicator that is optimized for convenient application of a biomedically useful adhesive composition to biological tissue. The known applicators are either optimized for delivery of other compositions or are inconvenient for the patient to use.

SUMMARY OF THE INVENTION

Because there is a need for an easy-to-use applicator for dispensing and applying biomedically useful compositions, the present invention provides a disposable applicator that can be used by a person, such as a patient, to apply such a composition conveniently, inexpensively, and effectively.

The applicator of the present invention is generally tubular in shape, having a single open distal end and a closed, sealed proximal end. Both ends are covered by an absorbent material, such as a sponge or foam. The applicator holds a biomedically useful liquid composition that can be dispensed and applied to a surface. The composition is maintained, until applied, in a frangible vial within the applicator. The liquid composition is dispensed through the open distal end only, and applied to the target site by wiping or rubbing the absorbent material covering the distal end on the site. The closed end is covered with an absorbent material that can be used prior to application of the liquid composition to dry the surface on which the liquid composition is to be applied.

The applicator is designed for simple and effective delivery of liquid compositions to target sites. The applicator is designed for single-handed use by a person with average strength, and requires little or no instruction prior to its use. The design is simple in construction (as compared to many applicators known in the art) and use, having no moving parts and requiring no special disposal procedures. Application of a biomedically useful composition contained within the applicator thus does not need to be supervised by a medical professional, but can be performed by the user in the environment, and at the time, chosen by the user.

BRIEF DESCRIPTION OF THE DRAWINGS

Reference will be made to the following drawings wherein like numerals refer to like elements and in which.

DETAILED DESCRIPTION OF PREFERRED EMBODIMENTS

Figure 1:
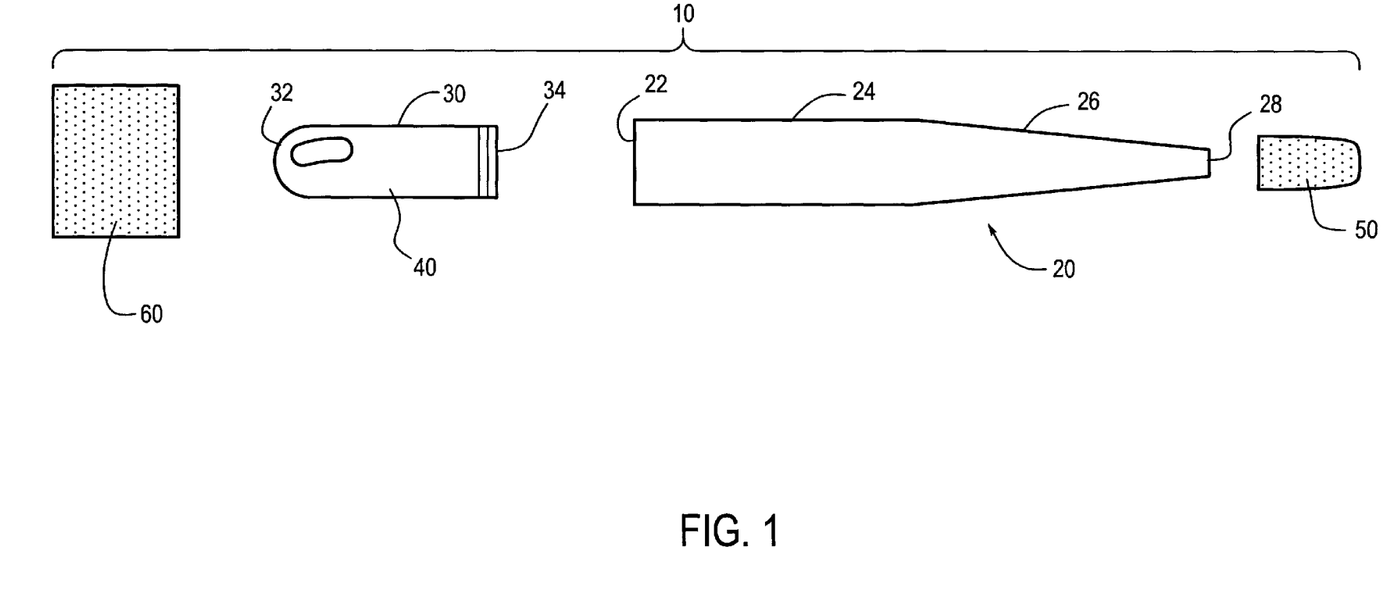
FIG. 1 is an exploded view of an applicator according to a first embodiment of the invention.
Figure 2:
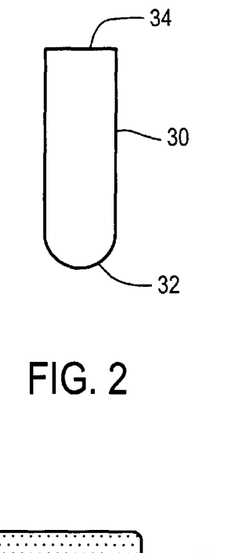
FIG. 2 is a side view of an open-ended material holding ampoule prior to filling.

With reference to FIG. 1, an applicator 10 according to a first embodiment is shown. Applicator 10 includes a hollow applicator body 20, preferably in the shape of an open-ended tube having a proximal end 22, a main body portion 24, a secondary body portion 26 and a distal end 28. A frangible ampoule 30 for holding a liquid material includes a closed end 32 and an initially open end 34. The frangible ampoule 30 retains a predetermined quantity of a dispensable material 40. An applicator swab 50 is provided on the distal end 28 of applicator body 20 and communicates with the opening of end 28. A dry wiping swab 60 is provided on the proximal end 22 of applicator body 20.

The applicator body should be flexible, relatively smooth and soft to the touch, without being slippery or otherwise difficult to pick up and hold. The material used to make the applicator body should be relatively inexpensive, and the applicator body should be easy to fabricate. Many materials suitable for use in fabricating the applicator body are known to those of ordinary skill in the art. For example, the applicator can be made of low density polyethylene or other such polymers. In preferred embodiments, the applicator body 20 is transparent or translucent.

Although depicted in FIG. 1 as having a tubular body that tapers nearly to a point at the distal end, the applicator body can have any suitable shape including, but not limited to, having an entirely tubular shape (constant cross-section from distal to proximal end), a flattened tubular shape, such that a cross-section appears elliptical or oval, a conical shape, and a flattened tubular shape that tapers toward the distal end.

Assembly of the applicator is described with reference to FIGS. 2–7, with a perspective view of the assembled applicator shown in FIG. 8. Frangible ampoule 30 is formed in a hollow, generally tubular shape from a suitable frangible material, including, but not limited to, plastic and glass. A preferred material is polyethylene terephthalate (PET). Ampoule 30 may be vial-shaped with a formed closed end 32 and an initially open end 34. Ampoule 30 can be any size. The size is chosen in conjunction with the quantity of the suitable dispensable material 40 and the desired fill capacity of the ampoule. The preferred ampoule 30 is tubular with an approximately 0.5 cm diameter and a length of about 1.27 cm. The preferred ampoule 30 has a wall thickness of between 0.0254 mm and 0.508 mm, preferably between 0.0508 mm and 0.254 mm, and more preferably between 0.0508 and 1.27 mm, and has a relatively long, stable shelf life of over two years. The frangible ampoule preferably contains a suitable amount of a liquid composition. For example, ampoule 30 can contain very small to very large amounts, such as, e.g., 0.6 ml, 1.0 ml, 1.5 ml, 2.0 ml, 5 ml, 10 ml, etc. However, the total volume of material contained within the anpoule can be any amount, and is determined based on the type of application for which the applicator is to be used and the desired size of the applicator to be used.

Figure 3:
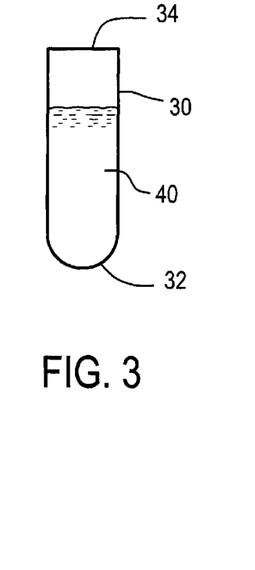
FIG. 3 is a side view of the material holding ampoule of FIG. 2 after filing with a desired liquid.
Figure 4:
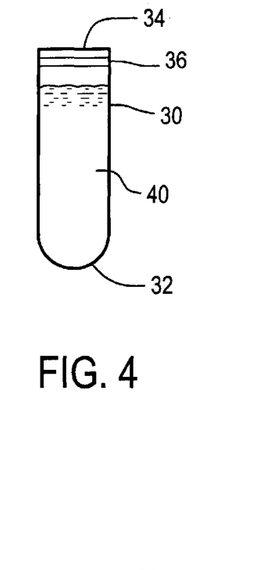
FIG. 4 is a side view of the material holding ampoule of FIG. 3 after sealing of the open end.

As shown in FIG. 3, the open ampoule 30 is filled with a predetermined amount of material. As shown, the amount of dispensable material preferably does not entirely fill the ampoule. Thus, a certain length of the ampoule at the initially open end 34 remains free to allow for sealing of end 34, after filling, by seal 36, as shown in FIG. 4. The sealing can be achieved by several sealing methods, such as ultrasonic welding or heat bonding. The method of sealing is chosen in conjunction with the material from which the ampoule is fabricated such that the ampoule is sealed without causing excessive damage to the ampoule material. Suitable sealing methods for the suitable ampoule materials are known to the skilled artisan. The design of the seal 36 may control the activation force if the sealed end is used as the frangible mechanism for ampoule 30. Thus, the body of the ampoule 30 is designed to withstand the activation force so that rupture controllably occurs at the seal on end 34. The ampoule should rupture upon application of a predetermined force. In a preferred embodiment, the force does not exceed 4.3 kg (9.5 lbs.), which is a force that can be readily exerted by a significant percentage of the male and female population.

Figure 5:
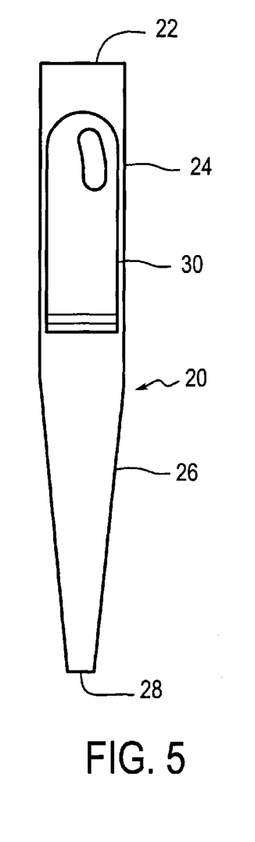
FIG. 5 is a side view of the material holding ampoule of FIG. 4 positioned within an open ended applicator tube according to the invention.

Once the ampoule is properly sealed, it can be inserted into hollow applicator body 20 as shown in FIG. 5. It is preferable to retain ampoule 30 within the main body portion 24, with the frangibly sealed end of ampoule 30 being adjacent secondary body portion 26 and oriented toward distal end 28. This retention is achieved in this embodiment by use of a main body diameter that is slightly larger than the diameter of ampoule 30 and a tapering secondary body portion that tapers to a diameter smaller than ampoule 30. A tapered secondary body portion also is beneficial as it funnels the material to a finer point at the distal end 28 so that more control of dispensing can be achieved. Alternatively, a stepped secondary body portion could be provided that limits the movement of the ampoule or the ampoule could be fixed within the main body portion by fixing means such as an adhesive.

A preferred applicator body 20 is tubular and has a diameter of between 0.82 and 0.96 cm and a length of approximately 10.8 cm. The secondary body portion 26 preferably tapers to a much smaller diameter of about 0.3 cm. The main body portion 24 has a length sufficient to retain ampoule 30. In embodiments, the main body portion 24 is about 5.1 cm long, and provides sufficient room between the retained ampoule 30 and the proximal end 22 to form a seal. Thus, in these embodiments for example, the secondary body portion may have a length of about 5.7 cm.

Figure 6:
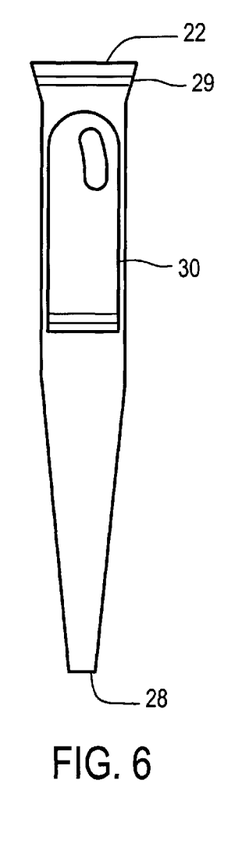
FIG. 6 is a side view of the applicator tube of FIG. 5 after sealing of the open end of the applicator tube.

After insertion of ampoule 30 into applicator body 20, the proximal end 22 of applicator body 20 is preferably sealed by seal 29. When the applicator body and the ampoule are fabricated from the same material, this sealing can be accomplished in the same manner as that performed to seal ampoule 30. Seal 29 at end 22 of applicator body 20 is not under any pressure as the distal end 28 of applicator body 20 is open. As such, end 22 will remain sealed even when sufficient pressure to rupture seal 36 of ampoule 30 is applied.

Figure 7:
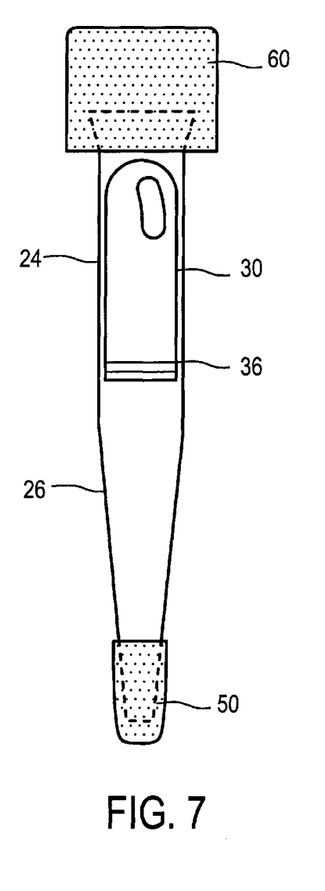
FIG. 7 is a side view of an assembled applicator after attachment of first and second swab members on ends of the applicator tube.

Next, swabs 50 and 60 are attached to ends of applicator body 20. Swab 60 is preferably a dry wiping swab attached to the sealed proximal end 22 of applicator body 20 by a fixing means such as adhesive. Alternatively, the swab could be friction fit or otherwise mechanically attached onto end 22. Swab 60 is preferably formed from an absorbent foam, such as thermoplastic polyurethane foam. A preferred foam is a hydrophilic polyurethane foam. A preferred swab 60 is generally rectangular (as fabricated), having a size of about 1.3 cm×1.0 cm×0.64 cm, although other sizes and shapes can be used depending on the desired application and the chosen shape of the applicator.

Swab 50 is preferably an applicator swab attached to open proximal end 28 by fixing means such as an adhesive or friction fit. Swab 50 is preferably formed from a soft, absorbent thermoplastic polyurethane foam. In some embodiments, to assist in proper application of the dispensed material, swab 50 can change colors when saturated with the dispensed material. Included in this color change is a darkening of the swab. This could be achieved using a clear liquid material and a swab that darkens when saturated with liquid. Alternatively, for example, changing color could be achieved by a white or other light colored swab and use of a darker colored dispensed material. To further assist in proper use of the applicator, swabs 50 and 60 can be color coded to readily identify ends of the applicator. Such color coding helps, for example, ensure that the user does not use the applicator swab as a drying swab. Each of swabs 50 and 60 can be any color and, although it is preferable that swabs 50 and 60 are lightly colored, such as white, the swabs are not limited to light colors. Furthermore, each of swabs 50 and 60 is preferably fabricated from very soft material so that the applicator can be used to apply biomedically useful compositions to sore, tender, or otherwise painful tissues.

Figure 8:
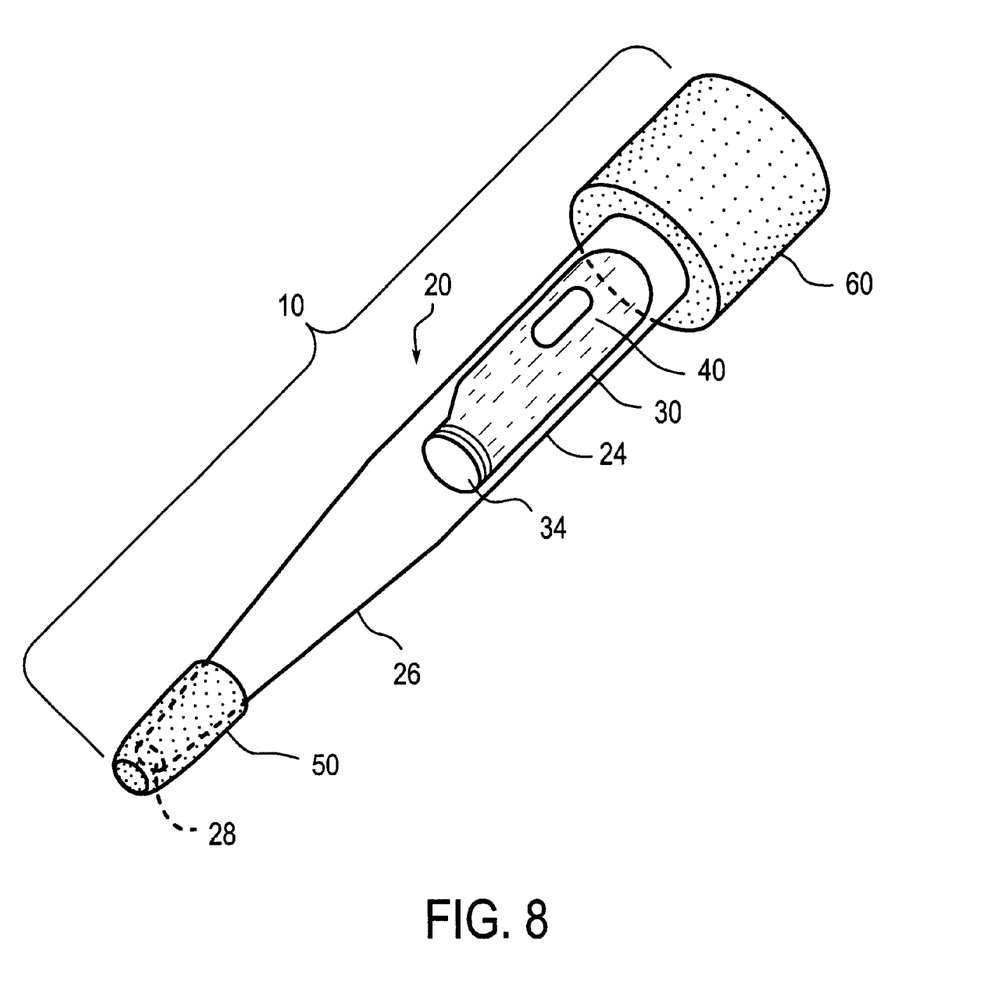
FIG. 8 is a perspective view of the applicator of FIG. 7 according to the first embodiment of the invention.

Now the assembly of applicator 10 is complete and an exemplary applicator is shown in FIG. 8. To prevent contamination of applicator 10, the applicator may be wrapped in a disposable covering. This may include, for example, a simple plastic heat sealed wrap, a shrink wrap, or a foil wrap depending on the application. The covering could also be made of paper. Such coverings are conventional and known to the skilled artisan. The overwrap functions as a dust cover, preventing foreign materials from contacting the swabs while in storage prior to use.

A preferred use of applicator 10 will now be described. The applicator is first removed from any wrapping or covering and held in one hand. Optionally, dry swab 60 is then rubbed or wiped across the surface to which the material within the applicator is to be applied. Then, the applicator 10 is grasped so that ampoule 30 is between the user's thumb and at least one other finger. Pressure is applied to the applicator body 20 at the site where ampoule 30 is located such that the pressure is transmitted through applicator body 20 to ampoule 30. Pressure is applied through pinching or squeezing between the two fingers until ampoule 30 breaks or opens. Continued squeezing forces liquid composition 40 within ampoule 30 to flow toward distal end 28. Controlled squeezing of the applicator body 20 causes the liquid 40 to wet applicator swab 50. Upon wetting, applicator swab 50 is used to apply the liquid composition to the desired site. Preferably, applicator swab is wetted to the point of saturation prior to application of the liquid. In embodiments, wetting to the point of saturation causes applicator swab 50 to change color, indicating to the user that application of pressure to applicator body 20 should be stopped. After use, the applicator 10 can be discarded.

Figure 9:
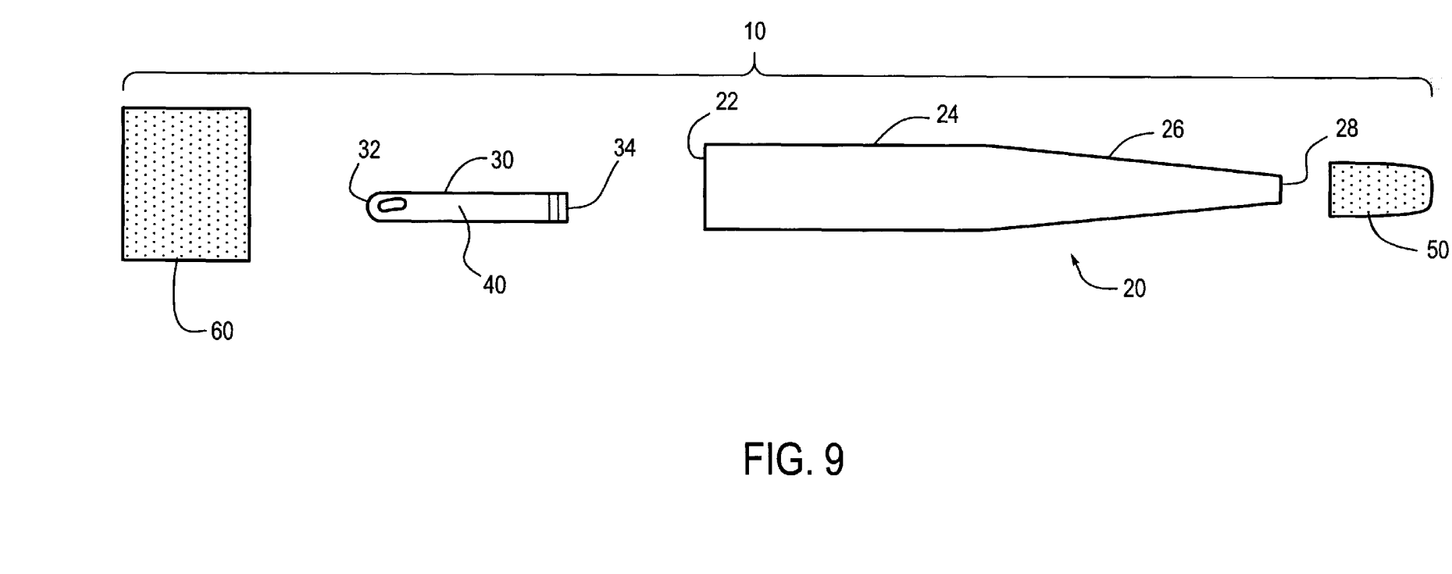
FIG. 9 is an exploded view of an applicator according to a second embodiment of the invention.
Figure 10:
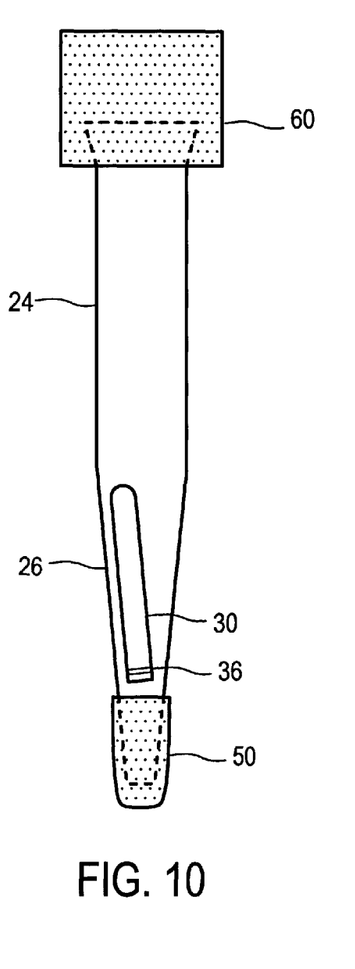
FIG. 10 is a top view of the applicator according to the second embodiment of the invention.
Figure 11:
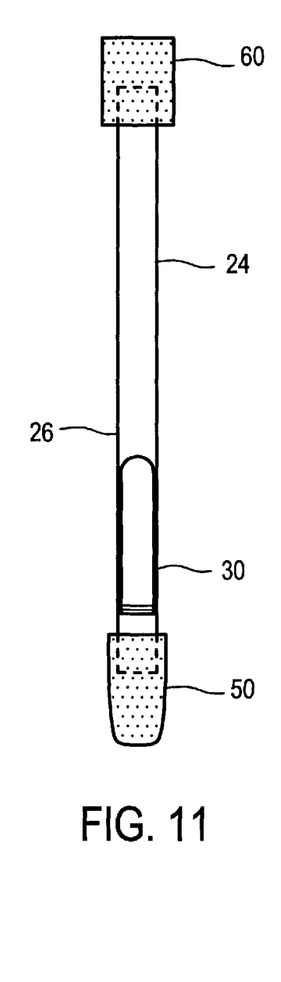
FIG. 11 is a side view of the applicator according to the second embodiment of the invention.

Another embodiment of the invention will now be described with reference to FIGS. 9–11. As shown in FIGS. 9–11, applicator 10 comprises hollow applicator body 20, which is preferably in the shape of an open-ended tube having a proximal end 22, a main body portion 24, a secondary body portion 26 and a distal end 28. The main body portion 24 has a generally elliptical or oval cross-section. The secondary body portion 26 has a generally elliptical or oval cross-section at its proximal end which tapers to form a circular cross-section at distal end 28. A frangible ampoule 30 is located and retained within secondary body portion 26 and includes a closed end 32 and an initially open end 34, and holds a predetermined quantity of a dispensable material 40. The frangible ampoule is retained in place in this embodiment by a mechanical interference fit. An applicator swab 50 is provided on the distal end 28 of applicator body 20 and communicates with the opening of end 28. A dry wiping swab 60 is provided on the proximal end 22 of applicator body 20.

The applicator of the second preferred embodiment has a generally elliptical or oval cross-section at main body portion 24 to provide a wider grip area for holding the applicator. The applicator of the second preferred embodiment is fabricated out of the same materials, and is used in the same manner, as the applicator of the first preferred embodiment, with the exception of the placement of frangible ampoule 30 within the applicator body. Placement of frangible ampoule 30 in the secondary body portion 26 provides exceptional convenience to the user because adjustment of the holding position (i.e., where the fingers grip the applicator) need not be changed once frangible ampoule 30 is broken.

In preferred embodiments, applicator 10 is used to apply a biomedically useful composition to a biological site. The biomedically useful composition can be any composition that has biomedical utility, including, but not limited to medicaments and/or adhesives.

Examples of medicaments include, but are not limited to antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof.

Exemplary medicaments include, but are not limited to, quaternary ammonium halides such as benzalkonium chloride and benzethonium chloride; chlorhexidine sulfate; gentamicin sulfate; hydrogen peroxide; quinolone thioureas; silver salts, including, but not limited to, silver acetate, silver benzoate, silver carbonate, silver chloride, silver citrate, silver iodide, silver nitrate, and silver sulfate; sodium hypochlorite; salts of sulfadiazine, including, but not limited to silver, sodium, and zinc salts; and mixtures thereof Preferable medicaments are those that are anions or help in radical generation or that are ion pairs or are themselves radicals.

In embodiments, the medicament is preferably a quaternary ammonium halide such as alkylbenzyldimethylammonium chloride (benzalkonium chloride; BAC) with an alkyl containing 6–18 carbon atoms, its pure components, or mixtures thereof, or benzethonium chloride; or a salt of sulfadiazine, such as a silver, sodium, or zinc salt.

In preferred embodiments, the applicator 10 is used to apply an α-cyanoacrylate composition to a site of tissue injury, such as a sore or lesion. In a preferred embodiment, the applicator is used to apply an α-cyanoacrylate composition to a stomatitis lesion. As used herein, stomatitis refers to an inflammation on the mucous tissue of the oral cavity, including lesions and sores.

In another embodiment, the present invention is directed to a method of treating a superficial or topical pathology, including, but not limited to a skin wound such as a superficial laceration, burn, or abrasion, or a sore on a mucous membrane. The method can comprise making an adhesive composition (40) optionally comprising a medicament, incorporating the composition into applicator 10, and applying the composition to a site to be treated with the applicator. In preferred embodiments, the site at which the composition is to be applied is first dried with drying swab 60. Preferably, the applicator is sterilized after fabrication, and more preferably, after any overwrapping has been included.

Alternatively, the method can comprise (a) applying a medicament (that can be a polymerization or cross-linking initiator, accelerator or inhibitor) to the affected tissue, (b) applying a polymerizable monomer-containing adhesive composition (40) over the medicament using applicator 10; (c) allowing the composition to polymerize; and (d) optionally, applying the composition at least once more to the same site. In preferred embodiments, the method comprises first drying the area at which the medicament and adhesive are to be applied with drying swab 60. Step (a) could be achieved by having the medicament on applicator swab 50.

Similarly, a polymerization or cross-linking initiator, accelerator or inhibitor can be included in the applicator, for example in applicator swab 50, on the inside of the open-ended tube, and/or the outside of the ampoule 30, in the absence or presence of a medicament.

Particular polymerization or cross-linking initiators, accelerators or inhibitors for particular monomers may be readily selected by one of skill in the art without undue experimentation. Control of the molecular weight distribution of the applied adhesive can be enhanced by selection of the concentration and functionality of the polymerization or cross-linking initiator, accelerator or inhibitor vis-a-vis the selected monomer and the desired effect (initiation, acceleration, or inhibition) that the polymerization or cross-linking initiator, accelerator or inhibitor is to have. Suitable polymerization initiators and polymerization or cross-linking initiators, accelerators or inhibitors for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; ascorbic acid; tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate, radical initiators and radicals, such as di-t-butyl peroxide and azobisisobutyronitrile; and bioactive compounds or agents.

In preferred embodiments, the polymerization or cross-linking initiator, accelerator or inhibitor may be a bioactive material, including quaternary ammonium halides such as alkylbenzyldimethylammonium chloride (benzalkonium chloride; BAC), its pure components, or mixtures thereof, especially those with an alkyl containing 6–18 carbon atoms; benzethonium chloride; and salts of sulfadiazine. Cobalt napthenate can be used as an accelerator for peroxide.

The polymerizable and/or cross-linkable material may also contain an initiator, accelerator or inhibitor that is inactive until activated by a catalyst or accelerator (also included within the scope of the term "polymerization or cross-linking initiator, accelerator or inhibitor" as used herein). Initiators, accelerators or inhibitors activated by stimulation such as heat and/or light (e.g., ultraviolet or visible light) are also suitable if the tip and/or applicator is appropriately subjected to such stimulation.

Suitable cyanoacrylate polymerization inhibitors or stabilizers include, but are not limited to, Lewis acids, such as sulfur dioxide, nitric oxide, boron trifluoride, and other acidic substances, including hydroquinone monomethyl ether, hydroquinone, nitrohydroquinone, catechol, and hydroquinone monoethyl ether, mixtures thereof and the like. Such inhibitors are disclosed in, for example, U.S. Pat. No. 3,559,652 to Banitt, the entire disclosure of which is incorporated herein by reference. The addition of these inhibitors and stabilizers inhibits premature polymerization of the monomer and slows down the rate of polymerization once the composition is in contact with the surface to be treated.

The polymerization or cross-linking initiator, accelerator or inhibitor is selected based primarily on the type of polymerizable or cross-linkable material contained within the ampoule. For example, the polymerization or cross-linking initiator, accelerator or inhibitor is selected to be compatible with and effective upon the polymerizable or crosslinkable material. Furthermore, the polymerization or cross-linking initiator, accelerator or inhibitor should be selected based on its relative effective rate in accordance with the particular use to be made of the adhesive composition. For example, if it is desired that the adhesive not polymerize or cross-link very quickly, a slower acting polymerization or cross-linking initiator or accelerator or an inhibitor may be selected. In contrast, if quick polymerization or cross-linking is desired, a faster acting polymerization or cross-linking initiator or accelerator may be selected.

In addition, it is also important to control the amount of polymerization or cross-linking initiator, accelerator or inhibitor incorporated into the applicator. For example, it is necessary to incorporate at least an effective amount of the polymerization or cross-linking initiator, accelerator or inhibitor into the applicator, such as on the outer surface of the frangible ampoule, so that upon breaking the frangible ampoule there is sufficient contact between the polymerizable or crosslinkable material and the polymerization or cross-linking initiator, accelerator or inhibitor for the polymerization or cross-linking initiator, accelerator or inhibitor to serve its intended purpose. However, there should not be so much polymerization or cross-linking initiator, accelerator or inhibitor present as to overly modify the rate and prevent operation of the applicator. For example, in the case of a polymerization or cross-linking initiator, accelerator or inhibitor being an initiator, there should not be so much initiator present as to fully polymerize or cross-link the polymerizable or cross-linkable material within the applicator, thereby clogging the applicator. Furthermore, it is preferred in embodiments that the polymerization or cross-linking initiator, accelerator or inhibitor not completely fill a space between the frangible ampoule and the applicator walls, such as by being at most only coated on the outer surface of the frangible ampoule, so as to permit space within the applicator for the polymerizable or cross-linkable material and the polymerization or cross-linking initiator, accelerator or inhibitor to mix.

Suitable film thickness for such topical applications is preferably between 1 and 10,000 $\mu$m, for example between 1 and 1000 $\mu$m.

In embodiments, the present invention provides a method of delivering a medicament to a tissue. The method can comprise making a composition comprising a medicament, applying the composition to a site using applicator 10, allowing the composition to polymerize, and maintaining the polymerized composition in contact with the site for a sufficient amount of time to allow the medicament to be delivered to the target site. Preferably, prior to application of the composition, the site at which application is to be performed is dried with drying swab 60.

Alternatively, the method of delivering a medicament to a tissue can comprise (a) applying a medicament (that can be a polymerization or cross-linking initiator, accelerator or inhibitor) to a site (e.g., directly to tissue); (b) applying a polymerizable monomer-containing composition over the medicament; and (c) optionally, applying the composition at least once more to the same site. Suitable film thickness and strength are preferably those disclosed above for other uses. Preferably, prior to application of the medicament, the site is dried with drying swab 60.

In embodiments, the dispensed liquid material comprises both an α-cyanoacrylate composition and a medicament, such as a drug. The medicament can be any suitable medicament known to those skilled in the art. In these embodiments, application of the composition provides not only protection for the affected area, but a secondary medical benefit as well. The medicament can, but does not need to, act to initiate and/or accelerate or inhibit polymerization and/or cross-linking of the monomer composition in addition to serving its medicinal function. The medicament may be in the form of a solid, such as a powder or a solid film, or in the form of a liquid, such as a watery, viscous, or paste-like material. The medicament may also be compounded with a variety of additives, such as surfactants or emulsifiers, and vehicles.

In embodiments, the medicament is released to the tissue to which it is in contact at a constant, or near constant, rate over a period of time while in contact with the affected tissue.

While use of the applicator is not restricted to any one application, it is particularly well suited for application of α-cyanoacrylate adhesive compositions to stomatitis lesions in a method of treating stomatitis. When used in this preferred method, the user (or patient) first removes the applicator from any overwrapping that is present. The drying swab 60 is then used to dry the affected area to remove saliva. The user then squeezes the applicator body at the frangible ampoule with sufficient force to break the ampoule. Continued squeezing of the applicator expresses the α-cyanoacrylate adhesive through distal end 28 and onto applicator swab 50. Applicator swab 50 is then brushed, swiped, or otherwise rubbed across the affected tissue to apply the adhesive. The adhesive is allowed to polymerize, thus providing a protective covering over the affected area.

In embodiments, the tissue immediately surrounding the affected area is dried with drying swab 60 along with drying of the affected area. In these embodiments, the α-cyanoacrylate composition can be applied to the surrounding, dry, unaffected tissue as well as to the affected tissue.

The present invention also provides a kit for providing the compositions to a user. In embodiments, the invention provides a kit for delivering a medicament to a patient. In this embodiment, the kit comprises applicator 10 holding a polymerizable monomer composition 40, such as an α-cyanoacrylate adhesive. The kit can also comprise another container holding a medicament. Alternatively, the kit can comprise one applicator holding a composition comprising both the adhesive and the medicament. In embodiments, multiple applicators and containers are present in the kit, each applicator holding one or more polymerizable monomers and each container holding one or more medicaments. Some applicators can hold mixtures of adhesives and medicaments. In a preferred embodiment, the kit comprises one applicator containing an adhesive and one container holding a medicament. In embodiments the kit is preferably sterilized.

The medicament is selected so that it is compatible with the co-packaged polymerizable monomer composition. In embodiments, the medicament can initiate polymerization and/or cross-linking of the monomer or modify (e.g., accelerate or inhibit) the rate of polymerization and/or cross-linking for the monomer to form a polymeric adhesive. Acceptable combinations of medicament and polymerizable monomer can be determined easily by one of skill in the art. The medicament is supplied in the kit in an amount that will be pharmaceutically effective when applied topically (i.e., directly to tissue, such as oral mucous tissue).

The amount of composition 40 within ampoule 30 can be a small quantity. Preferably, an adhesive composition is packaged in frangible ampoule 30 such that a suitable volume of the adhesive composition is present per applicator. Suitable volumes can be any amount that the ampoule can accommodate. For example, the ampoule 30 can be provided to contain very small to very large amounts such as, e.g., 0.1 ml, 0.6 ml, 1 ml, 1.5 ml, 2 ml, 5 ml, 10 ml, etc. While not necessary for most applications, the applicator (containing the adhesive) can be sterilized by appropriate means, including, but not limited to, dry heat sterilization, gamma irradiation, microwave irradiation, and electron beam irradiation.

In embodiments, the applicator containing the adhesive composition according to the invention is sterilized. Whatever method is chosen, it must be compatible with the composition to be sterilized. In embodiments where the composition is to be used for medical applications, the sterilized composition must show low levels of toxicity to living tissue during its useable life.

To be considered sterile, the composition within the applicator must show no bacterial growth after inoculation onto Soybean Casein Digest media, and incubation for 14 days at 32–35° C. Standard procedures and materials, such as those disclosed in USP XXIII <1211>, "Sterilization and Sterility Assurance of Compendial Articles" should be followed.

The liquid composition 40, in embodiments, is preferably a monomeric (including prepolymeric) adhesive composition. In embodiments, the monomer is a 1,1-disubstituted ethylene monomer, for example, an α-cyanoacrylate. Preferred monomer adhesive compositions of the present invention, and polymers formed therefrom, are useful as tissue adhesives, sealants for preventing bleeding or for covering open wounds, and in other absorbable and non-absorbable biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, and/or stomatitis); hernia repair; meniscus repair; and aiding repair and regrowth of living tissue. Other preferred monomer adhesive compositions of the present invention, and polymers formed therefrom, are useful in industrial and home applications, for example in bonding rubbers, plastics, wood, composites, fabrics, and other natural and synthetic materials.

Monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. No. 5,328,687 to Leung, et al., which is hereby incorporated in its entirety by reference herein.

Useful 1,1-disubstituted ethylene monomers include, but are not limited to, monomers of the formula:

$$HRC=CXY \qquad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include α-cyanoacrylates, vinylidene cyanides, C$_1$–C$_4$ alkyl homologues of vinylidene cyanides, dialkyl methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are α-cyanoacrylates. These monomers are known in the art and have the formula (II)

wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2-alkylene group having 2–4 carbon atoms, $R^5$ is an alkylene group having 2–4 carbon atoms, and $R^6$ is an alkyl group having 1–6 carbon atoms; or a group having the formula wherein n is 1–10, preferably 1–5 carbon atoms and $R^8$ is an organic moiety.

Examples of suitable hydrocarbyl and substituted hydrocarbyl groups include straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$–$C_8$ alkyl moieties, $C_2$–$C_8$ alkenyl moieties, $C_2$–$C_8$ alkynyl moieties, $C_3$–$C_{12}$ cycloaliphatic moieties, aryl moieties such as phenyl and substituted phenyl and aralkyl moieties such as benzyl, methylbenzyl, and phenylethyl. Other organic moieties include substituted hydrocarbon moieties, such as halo (e.g., chloro-, fluoro- and bromo-substituted hydrocarbons) and oxy-substituted hydrocarbon (e.g., alkoxy substituted hydrocarbons) moieties. Preferred organic radicals are alkyl, alkenyl, and alkynyl moieties having from 1 to about 8 carbon atoms, and halo-substituted derivatives thereof Particularly preferred are alkyl moieties of 4 to 6 carbon atoms.

In the cyanoacrylate monomer of formula (II), $R^3$ is preferably an alkyl group having 1–10 carbon atoms or a group having the formula —$AOR^9$, wherein A is a divalent straight or branched chain alkylene or oxyalkylene moiety having 2–8 carbon atoms, and $R^9$ is a straight or branched alkyl moiety having 1–8 carbon atoms.

Examples of groups represented by the formula —$AOR^9$ include 1-methoxy-2-propyl, 2-butoxy ethyl, isopropoxy ethyl, 2-methoxy ethyl, and 2-ethoxy ethyl.

The α-cyanoacrylates of formula (II) can be prepared according to methods known in the art. U.S. Pat. Nos. 2,721,858 and 3,254,111, each of which is hereby incorporated in its entirety by reference, disclose methods for preparing a-cyanoacrylates. For example, the α-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The α-cyanoacrylate monomers prepared with low moisture content and essentially free of impurities are preferred for biomedical use.

The α-cyanoacrylates of formula (II) wherein $R^3$ is a group having the formula $R^4$—O—$R^5$—O—$R^6$ can be prepared according to the method disclosed in U.S. Pat. No. 4,364,876 to Kimura et al., which is hereby incorporated in its entirety by reference. In the Kimura et al. method, the α-cyanoacrylates are prepared by producing a cyanoacetate by esterifiing cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoaciylate to form a high purity cyanoacrylate.

The α-cyanoacrylates of formula (II) wherein $R^3$ is a group having the formula can be prepared according to the procedure described in U.S. Pat. No. 3,995,641 to Kronenthal et al., which is hereby incorporated in its entirety by reference. In the Kronenthal et al. method, such α-cyanoacrylate monomers are prepared by reacting an alkyl ester of an α-cyanoacrylic acid with a cyclic 1,3-diene to form a Diels-Alder adduct which is then subjected to alkaline hydrolysis followed by acidification to form the corresponding α-cyanoacrylic acid adduct. The α-cyanoacrylic acid adduct is preferably esterified by an alkyl bromoacetate to yield the corresponding carbalkoxymethyl α-cyanoacrylate adduct. Alternatively, the α-cyanoacrylic acid adduct may be converted to the α-cyanoacrylyl halide adduct by reaction with thionyl chloride. The α-cyanoacrylyl halide adduct is then reacted with an alkyl hydroxyacetate or a methyl substituted alkyl hydroxyacetate to yield the corresponding carbaLkoxymethyl α-cyanoacrylate adduct or carbalkoxy alkyl α-cyanoacrylate adduct, respectively. The cyclic 1,3-diene blocking group is finally removed and the carbalkoxy methyl α-cyanoacrylate adduct or the carbalkoxy alkyl α-cyanoacrylate adduct is converted into the corresponding carbalkoxy alkyl α-cyanoacrylate by heating the adduct in the presence of a slight deficit of maleic anhydride.

Examples of monomers of formula (II) include cyanopentadienoates and acyanoacrylates of the formula:

(III)

wherein Z is —CH=$CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated in its entirety by reference.

Preferred α-cyanoacrylate monomers used in this invention are alkyl α-cyanoacrylates including octyl cyanoacrylates, such as 2-octyl α-cyanoacrylate; dodecyl cyanoacrylate; 2-ethylhexyl cyanoacrylate; methoxyethyl cyanoacrylate; 2-ethoxyethyl cyanoacrylate; butyl cyanoacrylates, such as n-butyl cyanoacrylate; ethyl cyanoacrylate; methyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. More preferred monomers are ethyl, n-butyl, and 2-octyl α-cyanoacrylate. Monomers utilized for medical purposes in the present application should be very pure and contain few impurities (e.g., surgical grade). Monomers utilized for industrial purposes need not be as pure.

The composition may also optionally include at least one stabilizing agent that inhibits polymerization. Such stabilizing agents may also include mixtures of anionic stabilizing agents and radical stabilizing agents.

Examples of suitable anionic stabilizing agents include, but are not limited to, (1) vapor phase anionic stabilizers such as sulfur dioxide, boron trifluoride, and hydrogen fluoride, and (2) liquid phase anionic stabilizers such as suflfric acid ($pK_a$–3.0); perchloric acid ($pK_a$–5); hydrochloric acid ($pK_a$–7.0); hydrobromic acid ($pK_a$–9); a sulfonic acid such as fluorosulfonic acid ($pK_a$<–10), chlorosulfonic acid ($pK_a$–10), and methanesulfonic acid; phosphoric acid ($pK_a$2.2); organic acids such as acetic acid ($pK_a$4.8), benzoic acid ($pK_a$4.2), chloroacetic acid ($pK_a$2.9), and cyanoacetic acid; and mixtures thereof. Each of the vapor phase and liquid phase anionic stabilizer is added to give a final concentration of less than 200 ppm. Preferably, each anionic stabilizer is present in a concentration of from about 5 to 80 ppm, more preferably 10 to 40 ppm. The amount of each anionic stabilizer to be used can be determined by one of ordinary skill in the art without undue experimentation. Suitable stabilizing agents can be found in copending U.S. application Ser. No. 09/099,457 to Malofsky et al., the entire disclosure of which is incorporated herein by reference.

Other anionic stabilizers include alkyl sulfate, alkyl sulfite, 3-sulfolene, allylsulfone, alkyl sulfoxide, mercaptan, and alkyl sulfide and mixtures thereof.

Combinations of at least one vapor phase stabilizer and at least one liquid phase anionic stabilizer are used. For example, combinations of sulfur dioxide and sulfuric acid, sulfur dioxide and perchloric acid, sulfur dioxide and chlorosulfonic acid, boron trifluoride and sulfuric acid, boron trifluoride and perchloric acid, boron trifluoride and chlorosulfonic acid, boron trifluoride and methanesulfonic acid, hydrogen fluoride and sulfric acid, hydrogen fluoride and perchloric acid, hydrogen fluoride and chlorosulfonic acid, and hydrogen fluoride and methanesulfonic acid can be used. A combination of boron trifluoride, sulfur dioxide, and sulfric acid can also be used, among other combinations. The two types of anionic stabilizers are chosen in conjunction such that the stabilizers are compatible with the chosen adhesive composition and each other stabilizer, as well as with the applicator and ampoule materials and the equipment used to make and package the composition and the medicament that is present (if one is present). In other words, the combination of vapor phase stabilizer(s), liquid phase stabilizer(s), and monomer should be such that a stabilized, substantially unpolymerized adhesive composition is present after packaging into frangible ampoule 30.

The composition may optionally include at least one plasticizing agent that imparts flexibility to the polymer formed from the monomer. The plasticizing agent preferably contains little or no moisture and should not significantly affect the stability or polymerization of the monomer. Such plasticizers are useful in polymerized compositions to be used for closure or covering of wounds, incisions, abrasions, sores or other applications where flexibility of the adhesive is desirable.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts up to 60 weight %, preferably up to 50 weight %, more preferably up to 30 weight %, and most preferably up to 10 weight % provides increased toughness and flexibility of the polymerized monomer over polymerized monomers not having plasticizing agents.

The composition may also optionally include at least one thixotropic agent. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The compositions of the invention comprise at least one radical stabilizing agent. Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole (BHA), butylated hydroxy toluene (BHT), t-butyl hydroquinone, and mixtures thereof. In embodiments, the amount of agents such as BHA is about 1,000–5,000 ppm.

Medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitrites; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium, and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines, and hydrazide.

Suitable proteins include collagen, gelatin, casein, soybean protein, vegetable protein, and keratin. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate, or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 to Perry, which is hereby incorporated in its entirety by reference. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A preferred formaldehyde scavenger for use in this invention is sodium bisulfite.

In practicing the present invention, the formaldehyde concentration reducing agent is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form. When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such bioerosion can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, poly-lactic acid, poly-1,4-dioxa-2-one, polyoxaltes, polycarbonates, copolymers of polyglycolic acid and poly-lactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly(anhydrides); poly(alkyl-2-cyanoacrylates); poly(dihydropyrans); poly(acetals); poly(phosphazenes); poly(urethanes); poly(dioxinones); cellulose; and starches.

Examples of surfactants which can be added to the mineral oil include those commercially available under the designations Triton X-100™ (Rohm and Haas), Tween 20™ (ICI Americas), and Tween 80™ (ICI Americas).

The composition may also optionally include at least one thickening agent. Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such cross-linking agents. Examples of suitable crosslinidg agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or polymerization or cross-linking initiator, accelerator or inhibitor may be added to initiate polymerization or to modify the rate of polymerization of the cyanoacrylate monomer/crosslinking agent blend.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2 -naphthalene-sulfonic acid (FD+C Yellow No. 6); 9(o-carboxyphenoyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)2,3-dihydro-3-oxo-1H-indole-5-sulfonic acid disodium salt (FD+C Blue No. 2); and [phthalocyaninato (2–)] copper.

Other compositions and additives contemplated by the present invention are exemplified by U.S. Pat. Nos. 5,624,669; 5,582,834; 5,575,997; 5,514,371; 5,514,372; and 5,259,835; and U.S. patent application Ser. No. 08/714,288, the disclosures of all of which are hereby incorporated in their entirety by reference.

What is claimed is:

1. A disposable applicator for dispensing and applying a material, comprising:
   an ampoule having a first closed end and a second frangibly sealed end, the ampoule having a length and a circumference and containing a predetermined quantity of a disposable material therein;
   a flexible applicator body having a hollow main applicator body portion with a sealed proximal end and a secondary applicator body portion with an open distal end, the main applicator body portion having a length and circumference sized to receive the ampoule therein, the second frangibly sealed end of the ampoule being positioned facing the secondary applicator body portion of the applicator;
   retaining means for retaining the ampoule substantially within the applicator body;
   a first swab attached to the proximal end of the main applicator body portion; and
   a second swab attached to and in fluid communication with the distal end of the secondary applicator body portion,
   wherein upon application of a sufficient force applied to the ampoule through the applicator body, the ampoule will controllably rupture at the second frangibly sealed end to form an open end to allow flow of the dispensable material through the open end toward the second swab.

2. The disposable applicator according to claim 1, wherein the ampoule is formed from a plastic material.

3. The disposable applicator according to claim 2, wherein the ampoule is formed from polyethylene terephthalate.

4. The disposable applicator according to claim 1, wherein the applicator body is formed from a plastic material.

5. The disposable applicator according to claim 4, wherein the applicator body is formed from a low density polyethylene.

6. The disposable applicator according to claim 1, wherein the applicator body is transparent or translucent.

7. The disposable applicator according to claim 1, wherein the main applicator body portion has a substantially constant cross-section and the secondary applicator body portion is tapered.

8. The disposable applicator according to claim 1, wherein the first swab is a dry swab formed from an absorbent material.

9. The disposable applicator according to claim 8, wherein the first swab is made of a thermoplastic polyurethane foam.

10. The disposable applicator according to claim 1, wherein the second swab is formed from an absorbent material.

11. The disposable applicator according to claim 10, wherein the second swab is formed from a thermoplastic polyurethane foam.

12. The disposable applicator according to claim 10, wherein the second swab is saturable with the dispensable material.

13. The disposable applicator according to claim 12, wherein the second swab changes color upon saturation with the dispensable material.

14. The disposable applicator according to claim 10, wherein the second swab includes a polymerization or cross-linking initiator, accelerator or inhibitor.

15. The disposable applicator according to claim 1, wherein the first and second swabs are of different colors.

16. The disposable applicator according to claim 1, wherein the frangible ampoule is frangible by an activation force of less than about 4.3 kg.

17. The disposable applicator according to claim 1, wherein the dispensable material is an α-cyanoacrylate adhesive composition.

18. The disposable applicator according to claim 17, wherein the α-cyanoacrylate is selected from the group consisting of n-butyl cyanoacrylate, 2-octyl cyanoacrylate, and mixtures of the two.

19. The disposable applicator according to claim 17, wherein the dispensable material further comprises a medicament.

20. A method of making a disposable applicator, comprising the steps of:
   providing an open-ended hollow ampoule;
   filling the ampoule with a desired amount of a dispensable material;
   sealing the open end of the ampoule to form a frangible sealed end of the ampoule that is more preferentially frangible than remaining portions of the ampoule such that rupture controllably occurs at the frangible sealed end;
   providing a hollow applicator body having a main applicator body portion with an open proximal end capable of receiving the ampoule and a secondary applicator body portion having a distal open end;
   inserting the ampoule fully into the main applicator body portion with the frangible sealed end of the ampoule facing the secondary applicator body portion;
   sealing the proximal end of the main applicator body portion;
   attaching an applicator swab to the open distal end of the secondary applicator body portion with the applicator swab in fluid communication with the open distal end of the secondary applicator body portion; and
   attaching a drying swab to the proximal end of the main applicator body portion.

21. The method according to claim 20, wherein the step of providing an applicator body includes providing a secondary applicator body portion having a body that tapers toward the distal end, the method further comprising the step of:
   retaining the ampoule substantially within the main applicator body portion by abutting the ampoule against the tapered secondary applicator body portion.

22. The method according to claim 20, wherein the step of filling fills the ampoule with a composition comprising an α-cyanoacrylate adhesive.

23. The method according to claim 22, wherein the α-cyanoacrylate is selected from the group consisting of n-butyl cyanoacrylate, 2-octyl cyanoacrylate, and a mixture of these two.

24. The method according to claim 22, wherein the composition further comprises a medicament.

25. The method according to claim 20, further comprising the step of providing a polymerization or cross-linking initiator, accelerator or inhibitor on the applicator swab.

26. The method according to claim 20, further comprising sterilizing the applicator.

27. The method according to claim 21, wherein the steps of providing an ampoule and an applicator body provide a transparent ampoule and a transparent applicator body, respectively.

28. The method according to claim 20, wherein the ampoule is made of a plastic material.

29. A method of treating tissue comprising:
provinding the applicator of claim 1, wherein the applicator holds a composition comprising an α-cyanoacrylate adhesive within the ampoule;
squeezing the applicator with sufficient force to break the ampoule;
squeezing the applicator to dispense the adhesive composition onto the second swab; and
applying the adhesive composition to desired tissue.

30. The method of claim 29, wherein the method further comprises the step of applying the adhesive composition to the tissue a second time.

31. The method of claim 29, wherein the method further comprises the step of drying the desired tissue with the first swab prior to applying the adhesive composition.

32. The method of claim 29, wherein the adhesive composition further comprises a medicament.

33. The method of claim 29, wherein the second swab contains a polymerization or cross-linking initiator, accelerator or inhibitor.

34. The method of claim 29, wherein the method is used to deliver a medicament to a tissue.

35. The method of claim 29, wherein the α-cyanoacrylate is 2-octyl cyanoacrylate.

36. The method of claim 29, wherein the applicator is used for a stomatitis pathology.

37. The method of claim 29, wherein the method further comprises the step of applying a medicament to the tissue prior to applying the adhesive composition to the tissue.

38. The method of claim 29, wherein the adhesive composition is applied to tissue immediately surrounding an area of pathology.

39. A kit comprising a saleable package containing the applicator of claim 1.

40. The kit of claim 39, further comprising a container holding a medicament.

41. The kit of claim 39, further comprising a medicament on the second swab.

42. The kit of claim 39, wherein the kit is sterilized.

43. A disposable applicator for dispensing and applying a material, comprising:
an ampoule having a first closed end and a second frangibly sealed end, the ampoule having a length and a circumference and containing a predetermined quantity of a dispensable 1,1-distributed ethylene adhesive composition therein;
a flexible applicator body having a hollow main applicator body portion with a sealed proximal end and a secondary applicator body portion with an open distal end, the main applicator body portion having a length and circumference sized to receive the ampoule therein, the second frangibly sealed end of the ampoule being positioned facing the secondary applicator body portion of the applicator;
retaining means for retaining the ampoule substantially within the applicator body;
a first swab attached to the proximal end of the main applicator body portion; and
a second swab attached to and in fluid communication with the distal end of the secondary applicator body portion,
wherein upon application of a sufficient force applied to the ampoule through the applicator body, the ampoule will controllably rupture at the second frangibly sealed end to form an open end to allow flow through the open end toward the second swab.

44. A method of making a disposable applicator, comprising the steps of:
providing an open-ended hollow ampoule;
filling the ampoule with a desired amount of a dispensable 1,1-disubstituted ethylene adhesive composition;
sealing the open end of the ampoule to form a frangible sealed end of the ampoule that is more preferentially frangible than remaining portions of the ampoule such that rupture controllably occurs at the frangible sealed end;
providing a hollow applicator body having a main applicator body portion with an open proximal end capable of receiving the ampoule and a secondary applicator body portion having a distal open end;
inserting the ampoule fully into the main applicator body portion with the frangible sealed end of the ampoule facing the secondary applicator body portion;
sealing the proximal end of the main applicator body portion;
attaching an applicator swab to the open distal end of the secondary applicator body portion with the applicator swab in fluid communication with the open distal end of the secondary applicator body portion; and
attaching a drying swab to the proximal end of the main applicator body portion.

* * * * *